US008435787B2

(12) United States Patent
Maguire et al.

(10) Patent No.: US 8,435,787 B2
(45) Date of Patent: May 7, 2013

(54) ALGINATE POLYELECTROLYTE ENCAPSULATION OF EMBRYONIC STEM CELLS (75) Inventors: Tim Maguire, Piscataway, NJ (US); Rene S. Schloss, East Brunswick, NJ (US); Martin L. Yarmush, Newton, MA (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 1326 days.

(21) Appl. No.: 11/919,407

(22) PCT Filed: May 9, 2006

(86) PCT No.: PCT/US2006/017968
§ 371 (c)(1),
(2), (4) Date: Jun. 13, 2008

(87) PCT Pub. No.: WO2006/122147
PCT Pub. Date: Nov. 16, 2006

(65) Prior Publication Data
US 2009/0311765 A1 Dec. 17, 2009

Related U.S. Application Data (60) Provisional application No. 60/679,310, filed on May 10, 2005.

(51) Int. Cl.
C12N 15/00 (2006.01)
(52) U.S. Cl.
USPC ............................ 435/382; 435/377; 435/383
(58) Field of Classification Search ........................ None
See application file for complete search history.

(56) References Cited

U.S. PATENT DOCUMENTS

| 5,290,684 | A | 3/1994 | Kelly |
| 5,738,876 | A | 4/1998 | Enevold |
| 2002/0155096 | A1 | 10/2002 | Chancellor et al. |
| 2003/0017510 | A1 | 1/2003 | Lee et al. |
| 2003/0113812 | A1 | 6/2003 | Hemperly |
| 2003/0119107 | A1 | 6/2003 | Dang et al. |

OTHER PUBLICATIONS

Wang et al. Proliferation and Differentiation of Mouse Embryonic Stem Cells in APA Microcapsule: A Model for Studying the Interaction between Stem Cells and Their Niche. Biotechnol. Prog. 2006, vol. 22, pp. 791-800.*
Zillberman et al. Polymer-encapsulated engineered adult mesenchymal stem cells secrete exogenously regulated rhBMP-2, and induce osteogenic and angiogenic tissue formation†.Polymer Polymers for Advanced Technologies. Polymer Advanced Technology, 2002, vol. 13, pp. 863-870.*
Chang et al. Growth of Recombinant Fibroblasts in Alginate Microcapsules. Biotechnology and Engineering. 1994, vol. 43, pp. 926-933.*
Dang et al. Controlled ES Cell Differentiation Cultures Stem Cells, May 1, 2004, vol. 22, pp. 275-282.*
Horak et al. Poly(2-hydroxyethyl methacrylate-co-ethylene dimethacrylate) as a Mouse Embryonic Stem Cells Support. J. Appliced Polmer Sci., 2002, vol. 87, pp. 425-432.*
Thomson et al. Embryonic Stem Cell Lines Derived from Human Blastocysts. Science, 1998, vol. 282, pp. 1145-1147.*
Dang et al., "Controlled, Scalable Embryonic Stem Cell Differentiation Culture", Stem Cells, 2004, 22:275-282.
Zimmermann et al., "Differentiation of murine and human chondrogenic cells encapsulated in UHV-alginate", http://www.biozentrum.uni-wuerzburg.de/fileadmin/REPORT/BIOTE/biote004.htm, (at least as early as Jan. 26, 2005).
Goosen, M.F., "Physico-Chemical and Mass Transfer Considerations in Microencapsulation", (1999) Ann. NY Acad. Sci. 875:84-104.
Magyar, J.P., et al., "Mass Production of Embryoid Bodies in Microbeads", (2001) Ann. NY Acad. Sci. 944:135-43.
Sun, et al., "Injectable microencapsulated islet cells as a bioartificial pancreas", (1984) Appl. Biochem. Biotechnol. 10: 87-99. (Abstract only).
N. Theise, "Liver Stem Cells: Prospects for Treatment of Inherited and Acquired Liver Diseases", Expert Opin. Biol. Ther. 3(3):403-408 (2003).
Tilles et al., "Bioengineering of Liver Assist Devices", J. Hepatobiliary Pancret Surg., 9:686-696 (2002).
Yarmush et al., "Assessment of Artificial Liver Support Technology", Cell Transplantation, 1(5):323-341 (1992).
Yarmush et al., "Hepatic Tissue Engineering Development of Critical Technologies", Ann NY Acad Sci., 665:238-252 (1992).
Zeilinger et al., "Time Course of Primary Liver Cell Reorganization in Three-Dimensional High-Density Bioreactors for Extracorporeal Liver Support: An Immunohistochemical and Ultrastructural Study", Tissue Engineering, 10 (7-8):1113-1124 (2004).
Caterson et al., "Polymer/Alginate Amalgam for Cartilage-Tissue Engineering", Ann. NY. Acad. Sci. 961:134-138 (2002).
Chan, et al., "Hepatic Tissue Engineering for Adjunct and Temporary Liver Support: Critical Technologies", Liver Transplantation, vol. 10, No. 11, 1331-1342 (2004).
Chan et al., "Metabolic Flux Analysis of Cultured Hepatocytes Exposed to Plasma", Biotechnol Bioeng 81: 33-49 (2003).
Dahlke et al., "Stem Cell Therapy of the Liver—Fusion or Fiction?", Liver Transplantation, vol. 10, No. 4, 471-479 (2004).
David et al., "In Vitro Assessment of Encapsulated C3A Hepatocytes Functions in a Fluidized Bed Bioreactor", Biotechnol. Frog., 1204-1212 (2004).
Demetriou, et al.,. "Prospective, Randomized, Multicenter, Controlled Trial of a Bioartificial Liver in Treating Acute Liver Failure", Annals of Surgery, vol. 239, No. 5, 660-670 (2004).

(Continued)

Primary Examiner — Deborah Crouch
(74) Attorney, Agent, or Firm — Fox Rothschild LLP; Gerard P. Norton; Wansheng Jerry Liu (57) ABSTRACT Alginate polyelectrolyte encapsulation is used for the controlled differentiation of embryonic stem cells. An isolated cell population is provided. The cell population includes a single cell suspension of ES cells encapsulated within an alginate polyelectrolyte microenvironment. The encapsulated ES cells are capable of differentiating within said microenvironment into hepatocyte lineage cells in the absence of embryoid body intermediates or growth factor supplementation.

32 Claims, 7 Drawing Sheets

OTHER PUBLICATIONS

Falasca et al., "Hepatocytes Entrapped in Alginate Gel Beads and Cultured in Bioreactor: Rapid Repolarization and Reconstitution of Adhesion Areas", Cells Tissues Organs, 168: 126-136 (2001).

Hamazaki et al., "Hepatic Maturation in Differentiating Embryonic Stem Cells in Vitro", FEBS Letters, 497, 15-19 (2001).

Hochleitner et al., "A Novel Bioartificial Liver with Culture of Porcine Hepatocyte Aggregates Under Simulated Microgravity", Artificial Organs, 29(1):58-66 (2005).

Rahman et al., "Alginate-Encapsulated Human Hepatoblastoma Cells in an Extracorporeal Perfusion System Improve Some Systemic Parameters of Liver Failure in a Xenogeneic Model", Artificial Organs 28(5):476-482 (2004).

Rokstad et al., "Evaluation of Different Types of Alginate Microcapsules as Bioreactors for Producing Endostain", Cell Transplantation, vol. 12, 351-364 (2003).

Selden et al., "Comparison of Three Solid Phase Supports for Promoting Three-Dimensional Growth and Function of Human Liver Cell Lines", Artificial Organs, 22(4):308-319 (1998).

Shito et al., "Efficacy of an Extracorporeal Flat-Plate Bioartificial Liver in Treating Fulminant Hepatic Failure", Journal of Surgical Research, 111, 53-62 (2003).

Susick, et al., "Hepatic Progenitors and Strategies for Liver Cell Therapies", Ann NY Acad. Sci., 944:398-419 (2001).

Theise, et al., "Liver from Bone Marrow in Humans", Hepatology, 32:11-16 (2002).

Tilles et al., "Critical Issues in Bioartificial Liver Development", Technology and Health Care, 10:177-186 (2002).

van de Kerkhove et al., "Clinical Application of Bioartifical Liver Support Systems", Ann Surg., 240:216-230 (2004).

Vessey et al., "Hepatic Stem Cells: A Review", Pathology, 33:130-141 (2001).

Viravaidya et al., "Development of a Microscale Cell Culture Analog to Probe Naphthalene Toxicity", Biotechnol. Prog. 20:316-323 (2004).

Xu et al., "Characterisation of Some Cytotoxic Endpoints Using Rat Liver and HepG2 Spheroids as in Vitro Models and their Application in Hepatotoxicity Studies. II. Spheroid cell Spreading Inhibition as a New Cytotoxic Marker", Toxicology and Applied Pharmacology, 189:112-119 (2003).

* cited by examiner

Figure 7

ALGINATE POLYELECTROLYTE ENCAPSULATION OF EMBRYONIC STEM CELLS

FIELD OF THE INVENTION

The present invention relates to alginate polyelectrolyte microencapsulation of cells. In particular, the invention is directed to the use of alginate poly-L-lysine microencapsulation in the controlled differentiation of embryonic stem cells.

BACKGROUND

A stem cell is a cell that has the ability to replicate itself for indefinite periods and to give rise (differentiate), under suitable conditions, to the many different cell types that make up an organism. That is, stem cells have the ability to develop into mature cells that have characteristic morphology and specialized functions, such as liver cells, heart cells, skin cells, nerve cells, etc.

Embryonic stem (ES) cells are able to differentiate into virtually all cell and tissue types of an organism—in vivo as well as in vitro. Unlike other stem cells, they can differentiate into cells that are derived from all three primary germ layers: the ectoderm, mesoderm or endoderm. Each cell type and tissue type in an adult organism originates from these three primary germ layers. For example, the endoderm is the source of epithelial cells lining respiratory passages and the gastrointestinal tract and gives rise to the pharynx, esophagus, stomach and intestine and many glandular tissues and organs, including salivary glands, liver, pancreas and lungs.

The development of effective tissue-engineered artificial liver devices, generated from autogenic or allogeneic cells, has been limited by the absence of large numbers of mature, functional hepatocytes. Such artificial liver devices can be used, for example, as a true alternative to liver transplantation.

Also, devices employing functional hepatocytes can be used as in vitro systems for pharmaceutical toxicology studies, and as biosensors for environmental toxins. However, the development of these devices has similarly been limited by the absence of large numbers of mature functional hepatocytes.

Recently, considerable effort has been directed towards incorporating adult and embryonic stem cell differentiation strategies into the generation of a renewable hepatocyte cell source (1, 2, 3, 4 and 5). Although several publications have described techniques to effectively differentiate stem cells into hepatocytes (6), these prior techniques have been limited in a number of ways. Such limitations include the absence of large scale processing considerations, incomplete downstream enrichment techniques, and ineffective long term maintenance of functional hepatocytes. Thus, a culture environment that is controllable, scalable and reversible may alleviate the practical limitations of effectively differentiating stem cells into hepatocytes.

In the past, scalable, controlled culture systems have been generated with alginate poly-L-lysine (PLL) encapsulation (7, 8 and 9). The benefits of encapsulating cells in alginate are numerous. First, alginate encapsulation is reversible. For example, polymerized alginate beads can be contacted with divalent cation chelators to depolymerize the alginate. This facilitates rapid cell recovery for downstream analysis and application. Second, alginate encapsulation, through variations in the encapsulation process (e.g., alginate concentration, alginate composition, PLL concentration, bead diameter, and cell seeding density), can discretely control key culture parameters.

Prior to the present invention, it was believed that full differentiation potential of ES cells could only be achieved if the ES cells were forced to differentiate both by morphological cues (embryoid body [EB] formation), as well as by growth- and differentiation-inducing factors. It was known that microencapsulated ES cells can grow as compact colonies within alginate beads and give rise to morula-like structures and subsequently to embryoid bodies. Previous investigators focused on large-scale production of embryoid bodies in alginate microbeads, with subsequent induction of differentiation into a specific cell type (e.g., cardiomyocytes) in adhesion cultures. A disadvantage of this approach was that it was necessary to release the compact colonies of ES cells from the microbeads before differentiation in adhesion cultures could be induced. Also, it was necessary to culture the bead-released ES cell colonies in the presence of retinoic acid to induce differentiation.

Since the aim is to establish a method suitable for the large-scale differentiation of ES cells into specific cell types, differentiation within the beads is desirable. For example, this permits a specific cell type to be recovered in a small culture volume.

Before the present invention, approaches to differentiate ES cells into specific cell types within alginate beads had limited success and had practical limitations. For example, previously, differentiation of ES colonies within 1.1% alginate microbeads, which had weak mechanical resistance, could only be promoted by supplementation of the cell media with retinoic acid, and required the cumbersome formation of embryoid bodies. Also, only some of the cystic embryoid bodies within the beads appeared to differentiate into a specific cell type.

In view of the foregoing, it would be advantageous if alginate microencapsulation could be used as a tissue culture environment for the controlled differentiation of embryonic stem cells within the alginate beads. It would also be advantageous to provide a system in which the beads have good mechanical resistance, and in which differentiation within the beads is possible in absence of growth factors, and in absence of embryoid body intermediates.

SUMMARY OF THE INVENTION

The present invention provides an isolated cell population including a single cell suspension of embryonic stem cells (ES cells) encapsulated within an alginate polyelectrolyte microenvironment, wherein the encapsulated ES cells are capable of differentiating within this microenvironment into hepatocyte lineage cells in the absence of embryoid body intermediates or growth factor supplementation.

The invention further provides a method for promoting differentiation of embryonic stem cells (ES cells) into functional hepatocytes. The method includes encapsulating a single cell suspension of ES cells within an alginate polyelectrolyte microenvironment. The method also includes culturing the encapsulated cells in differentiation cell media; and allowing the encapsulated ES cells to differentiate into hepatocyte lineage cells in the absence of embryoid body intermediates or growth factor supplementation.

Also provided is a method for producing encapsulated embryonic stem (ES) cells. The method includes providing a single cell suspension of ES cells; and combining the single cell suspension of ES cells with an alginate solution to form a mixture. The method also includes subjecting the mixture to an electrostatic field to form electrostatic alginate droplets; and exposing the electrostatic alginate droplets to a divalent cation solution to form a bead about the ES cells. Moreover, the method includes allowing the bead to polymerize in the presence of the divalent cation solution; and contacting the polymerized bead with a polyelectrolyte solution.

The present invention further provides a method for maintaining a hepatocyte differentiated state. The method includes culturing encapsulated single embryonic stem cells (ES cells) in differentiation cell media, wherein the encapsulated ES cells are encapsulated within an alginate polyelectrolyte microenvironment. The method also includes allowing the cultured encapsulated ES cells to differentiate into hepatocyte lineage cells in the absence of embryoid body intermediates or growth factor supplementation; and maintaining the hepatocyte differentiated state of the cells by maintaining the encapsulated differentiated cells in the differentiation cell media.

Further provided is a method for increasing the yield of embryonic stem cells. The method involves encapsulating a single cell suspension of ES cells within an alginate polyelectrolyte microenvironment including a polymerized bead formed at an alginate concentration of from about 1.7% (w/v) to about 2.5% (w/v). The method also involves culturing the encapsulated cells in cell media including a differentiation inhibitory factor to maintain an undifferentiated phenotype for the encapsulated cells; and allowing the encapsulated undifferentiated ES cells to expand in culture while in the presence of the differentiation inhibitory factor.

The present invention also provides a kit. The kit includes single embryonic stem cells (ES cells) encapsulated within an alginate polyelectrolyte microenvironment, wherein the encapsulated single ES cells are capable of differentiating within this microenvironment into hepatocyte lineage cells in the absence of embryoid body intermediates or growth factor supplementation.

BRIEF DESCRIPTION OF THE DRAWINGS

FIG. 2 (A and B) are graphs showing the comparison of viability (A) and growth kinetics (B) in encapsulated undifferentiated embryonic stem cells and Hepa1-6 cells after they were cultured in DMEM media containing ESGRO to prevent differentiation.

FIG. 3 (A and B) are graphs showing the urea secretion (A) and intracellular albumin levels (B) in encapsulated undifferentiated embryonic stem cells and Hepa1-6 cells after they were cultured in DMEM media containing ESGRO to prevent differentiation. Panels C and D depict monolayer Hepa 1-6 urea secretion and intracellular albumin levels, respectively.

FIG. 4 (A and B) are graphs showing viability (A) and growth kinetics (B) in an encapsulated embryonic stem cell population after the encapsulated cells were cultured in Iscove's media (an LIF-free media).

FIG. 5 (A and B) are graphs showing urea secretion (A) and intracellular albumin levels (B) in encapsulated embryonic stem cells after the encapsulated cells were cultured in Iscove's media. Panels C and D depict the embryoid body control for urea and intracellular albumin production, respectively.

FIG. 6 (A and B) are graphs showing the modulation of cellular function through changes in cell seeding density at day 20 post encapsulation of embryonic stem cells. The encapsulated cells were cultured in Iscove's media. Both urea secretion (A) and intracellular albumin production (B) were evaluated as a function of cell seeding density.

FIG. 7 (A and B) are graphs showing the modulation of cellular function through changes in alginate concentration at day 20 post encapsulation of embryonic stem cells. The encapsulated cells were cultured in Iscove's media. Both urea secretion (A) and intracellular albumin production (B) were evaluated as a function of alginate concentration.

DETAILED DESCRIPTION OF THE INVENTION

The terms "differentiation", "differentiate" and the like are known in the art. The meaning is intended to include the potential of any and all types of stem or progenitor cells to produce more specialized or mature or committed progeny cells.

The term "differentiation inhibitory factor" and the like is a substance which acts to maintain an undifferentiated phenotype of cells.

The term "differentiation cell media" is a cell media that promotes differentiation of cells (e.g., stimulates them to become committed to a desired cell lineage, such as a hepatocyte-lineage cell.

The term "growth factor" as used herein is intended to mean a substance that is involved in cell differentiation and growth. The term is meant to include any regulator substance in morphogenesis.

The term "embryoid bodies" is known in the art and is intended to mean aggregates of cells derived from embryonic stem cells. Upon aggregation, differentiation is initiated.

Conventional molecular biological or cell biological techniques are disclosed, for example, in the following references: "Current Protocols in Molecular Biology" vols. I-III (F. Ausubel, Ed. 1994); "Cell Biology: a Laboratory Handbook" vols. I-III (J. E. Cellis, Ed. 1994); "Animal Cell Culture" (R. I. Freshney, Ed. 1986). The molecular biological and cell biological techniques disclosed in these references are incorporated herein by reference.

Cells

According to the present invention, an isolated cell population is provided. This cell population includes a single cell suspension of embryonic stem cells (ES cells) encapsulated within an alginate polyelectrolyte microenvironment. The encapsulated ES cells are capable of differentiating within this microenvironment into hepatocyte lineage cells in the absence of embryoid body intermediates or growth factor supplementation. The alginate encapsulation provides a scaleable and reversible tissue culture environment useful to promote embryonic stem cell differentiation into hepatocytes.

In one embodiment of the present invention, the alginate polyelectrolyte microenvironment includes poly-L-lysine (PLL). In a further embodiment of the present invention, the alginate polyelectrolyte microenvironment includes a divalent cation. Suitable divalent cations include $Ca^{2+}$ or $Ba^{2+}$.

It is preferred that the encapsulated embryonic stem cells are from a mammalian species. Mammals include laboratory animals, such as rats, mice, and rabbits; farm animals, such as cows, pigs, horses, and sheep; pet animals, such as dogs and cats; and primates, such as monkeys, orangutans, apes and humans. The preferred mammals include mice or humans.

Prior to the present invention, it was not known to use alginate-polyelectrolyte encapsulation (e.g., alginate-poly-L-lysine encapsulation) to control the differentiation of suspended ES cells into mature hepatocytes within the alginate beads.

The present invention has numerous advantages. For example, differentiation into hepatocyte lineage cells occurs without the cumbersome step of embryoid body formation, and without growth factor supplementation. Also, since the aim is to establish a method suitable for large-scale differentiation of ES cells into specific cell types, differentiation within the alginate polyelectrolyte microenvironment (i.e., within the alginate beads) is desirable. This promotes a specific cell type to be recovered in a small culture volume. In addition, the encapsulation may be reversed, allowing for easy cell recovery for downstream analysis and application. The encapsulation parameters may also be modified so as to modulate cellular function, as described in the Examples section of the present application.

The encapsulated ES cells are desirably positive for a cell surface marker selected from the following: SSEA4, Tra-1-60, Tra-1-81, Oct-4 and combinations thereof. Stem cell surface markers are described, for example, in Carpenter, et al. (2003) Cloning Stem Cells. 5(1): 79-88.

As described above, the encapsulated ES cells are capable of differentiating within the alginate beads into hepatocyte lineage cells. The hepatocyte lineage cells may be characterized by cell-surface or functional markers.

In one embodiment, the hepatocyte lineage cells may be positive for a cell surface marker selected from the following: CD34, CD38, C-kit and combinations thereof. Such hepatocyte surface markers are described, for example, by Tanabe, et al. in Biochem. Biophys. Res. Commun. (2004) Nov. 12, 324 (2): 711-8.

In other embodiments, the hepatocyte lineage cells may produce albumin and/or may secrete urea. In another embodiment, the hepatocyte lineage cells may express a polypeptide selected from the following: cytochrome P450 subunit 1a1, cytochrome P450 subunit 1a2, cytochrome P450 subunit 1b1, cytochrome P450 subunit 2b9, cytochrome P450 subunit 2b13, cytokeratin 18, connexin 32, alpha-fetoprotein, transthyretin, alpha-1-antitrypsin, tyrosine aminotransferase and combinations thereof. Such indicators of hepatocyte functions are described by Arias, et al. in the "Liver Biology and Pathobiology", 4$^{th}$ edition. (2001) Philadelphia: Lippincott, Williams and Wilkins.

The alginate polyelectrolyte microenvironment described herein provides a biocompatible tissue culture environment for embryonic stem cells, as well as hepatocytes. In particular, as described in the Examples section, neither the encapsulation, nor the depolymerization/recovery process significantly reduced cell viability. Furthermore, greater than 90% viability was maintained over the entire 20-day experimental period, as shown in the Examples section. This indicated the ability to use the alginate-polyelectrolyte encapsulation described herein for long-term culture configurations.

In one embodiment of the present invention, the alginate polyelectrolyte microenvironment may be in the form of a polymerized bead. In another embodiment, the bead is formed at a cell seeding density of about $1 \times 10^6$ cells/ml to about $1 \times 10^7$ cells/ml. In one preferred embodiment, the bead is formed at a cell seeding density of about $5 \times 10^6$ cells/ml.

With respect to the alginate concentration, the bead may be formed at an alginate concentration of from about 1.7% (w/v) to about 2.5% (w/v). In one particular embodiment, the bead is formed at an alginate concentration of about 2.0% (w/v).

One suitable bead size is about 500 μm. In one desired embodiment, beads may be initially formed at a cell seeding density of $5 \times 10^6$ cells/ml, and a 2.0% alginate concentration. An applied voltage of 6.5 kV is also preferably used. These parameters led to a bead size of 500 μm. However, the present invention is not limited to these particular parameters.

The present inventors have characterized their bead system, including functional assessment of both encapsulated undifferentiated ES cells (cultured in the presence of LIF) and hepatoma cells (hepatocytes). In particular, the present inventors observed that although encapsulated ES cells cultured with LIF continued to divide at the same rate as hepatocytes, the encapsulated cells did not express hepatocyte function. Therefore, in one embodiment, the alginate polyelectrolyte microenvironment of the encapsulated ES cells does not promote hepatocyte function in undifferentiated ES cells. This is noteworthy because it indicates that no transport limitations exist for LIF in the encapsulation system.

As described above, the encapsulated ES cells are capable of differentiating within the alginate polyelectrolyte microenvironment into hepatocyte lineage cells. In one embodiment, the alginate polyelectrolyte microenvironment promotes hepatocyte function in hepatocyte differentiated ES cells. Thus, not only do the alginate-polyelectrolyte beads promote ES cell differentiation into the hepatocytes following LIF removal from the media, the beads also support hepatocyte function. In particular, with reference to the Examples section, the present inventors have demonstrated that encapsulated ES cells increased both urea secretion and intracellular albumin production during the 20-day culture period, with maximum functional expression observed in the present study occurring at day 20. It is noted that the values obtained for urea secretion and intracellular albumin production were comparable to an embryoid body culture formed using the hanging drop technique.

In one embodiment, at least 80% of the cell population of the present invention is capable of differentiating into the hepatocyte lineage cells within the alginate polyelectrolyte microenvironment. Although this differentiation efficiency is similar to that in traditional differentiation systems, such as the hanging drop technique, the encapsulation system of the present invention presents significant advantages. For example, it is more amenable to scale-up protocols. Furthermore, the instant encapsulation system may use a single cell suspension, thus bypassing the formation of an embryoid body core, which was known to make cellular isolation difficult and lead to large mixed cell populations.

Furthermore, the encapsulation system of the present invention does not require the addition of growth factor or extracellular matrix protein supplementation. This is different from prior systems, which have induced hepatocyte differentiation from ES cells via hepatocyte specific mediator addition. In these prior systems, the hepatocyte specific mediators clearly played a key role in hepatocyte differentiation. This was disadvantageous since the stem cells were induced to differentiate only when in the presence of the right combination of molecules and cell conditions, which could be difficult to identify.

A further advantage of the present invention is that the embryonic stem cells are reversibly encapsulated. As described above, this allows for easy cell recovery for downstream analysis and biotechnological applications. In one embodiment, the bead is polymerized in the presence of a divalent cation solution. In another embodiment, the beads may be depolymerized in the presence of chelating agent. For example, a chelating agent, such as sodium citrate, may be used to induce depolymerization of the beads. This is described in Example 1.

The emergence of hepatocyte-based clinical and pharmaceutical technologies, such as bioartificial liver support systems, in vitro drug screening systems, and environmental biosensors, has been limited in the past by the lack of suitable and readily available hepatocyte sources. The present inventors have found that the alginate microenvironment herein described is biocompatible, is conducive to ES cell differentiation, and allows for the maintenance of differentiated cellular function. The scaleable differentiation system herein described provides an effective step toward addressing the need for scaleable stem cell differentiation systems.

As described above, the cell population of the present invention is capable of differentiating into hepatocyte lineage cells. In one embodiment, the hepatocyte lineage cells may be incorporated into a bioartificial liver device. For example, cells of the present invention may be used in any of the bioartificial liver devices described in references 10-19.

In another embodiment, the hepatocyte lineage cells may be incorporated into a biosensor for detection of environmental toxins. For example, cells of the present invention may be used in a biosensor such as that described in reference 20.

In yet another embodiment the hepatocyte lineage cells may be incorporated into a system for pharmaceutical toxicology screening. An example of an in vitro system for pharmaceutical toxicology screening, which may incorporate the cells of the present invention, is disclosed, for example, in reference 21.

It is contemplated that the hepatocyte lineage cells may be incorporated into effective extracorporeal bioartificial liver devices, biosensors for environmental toxins, or in vitro systems for pharmaceutical toxicology studies in an encapsulated form. Alternatively, the alginate encapsulation may be first reversed using divalent cation chelators to depolymerize cross-linked beads, and following cell recovery, the hepatocyte lineage cells may be analyzed and used in one of the aforementioned clinical or pharmaceutical applications.

It is well within the contemplation of the present invention that the ES cells or the hepatocyte-lineage cells derived from the ES cells may be genetically modified to contain an expression vector. The expression vector may include one or more heterologous genes which can be expressed and whose expression products are produced at the site at which the cells are applied or introduced in vivo or in vitro.

For example, the ES cells or hepatocyte-lineage cells may be genetically engineered to contain one or more nucleic acid sequences encoding one or more active biomolecules or indicator molecules. Examples of such molecules include proteins, polypeptides, peptides, hormones, metabolites, drugs, enzymes, and the like. Such molecules may be useful for tissue regeneration and reconstitution. These molecules may also be useful to deliver a gene product, such as a therapeutic agent, e.g., hormone or factor, to a tissue or organ site.

A bioindicator molecule, such as an enzyme, or an antibiotic, may be present in the ES cells or hepatocyte-lineage cells for the purpose of selection of cells containing the vector construct. Such a bioindicator molecule may be an inducible or noninducible gene and will generally allow for positive selection under induction, or without induction, respectively.

Moreover, an indicator biomolecule, e.g., hormone, metabolite, or enzyme, may be a useful indicator of drug toxicity in situations where the hepatocytes are incorporated into a drug toxicity screening system. Drug toxicity may also be assessed by assessing cell viability. Methods for assessing cell viability are well known in the art.

The hepatocyte-lineage cells may be combined with a polymeric matrix, if desired. For example, these cells may be admixed with, attached to, introduced into, or applied to, a polymeric matrix, such as a microporous polymeric membrane or hollow polymer fibers. These types of polymeric matrices may be used, for example, in bioartificial liver devices, biosensors for environmental toxins and pharmaceutical toxicology screening systems.

The hepatocyte lineage cells may be combined with a polymeric matrix by any number of methods known to those having skill in the art. For example, inoculation may be used if the polymeric matrix comprises a solid or semi-solid material which does not readily mix with cells in suspension. In another example, a suspension of the cells may be mixed with a suitable biological or synthetic adhesive (bioadhesive) matrix, and the combination can be spread, sprayed, painted, or otherwise applied onto a polymeric matrix, or onto a tissue or organ site. A cell-bioadhesive combination may be applied by spreading, painting or coating using a spreading or coating device, such as a small brush, spatula, knife, or other device suitable for medically coating a surface, such as a surface of a polymeric matrix or a tissue or organ surface. In addition, compressed air may be used to spray or foam a cell-bioadhesive mixture or suspension onto a wound, biological surface, or a polymeric matrix surface. In another aspect of the invention, the cells may be attached to, introduced to, or applied to a polymer matrix or biological surface using a biological adhesive (bioadhesive), such as, but not limited to, fibrin glues or gels.

For example, with respect to a drug toxicity device, cells recovered following depolymerization of the beads can be seeded to a variety of different sized culture plates (24 well, 48 well, 96 well) on a variety of substrates (collagen, fibronectin, matrigel) and can be maintained in a differentiation media (e.g., Iscove's Media, LIF-free). These plates can then be supplemented with the drug that is being tested, and changes in hepatocyte function such as albumin production, urea secretion, and cytochrome p450 analysis can be monitored.

With respect to environmental biosensors, cell recovered following depolymerization can be seeded to the surface of an environmental biosensor. Thereafter, changes in hepatocyte function can be monitored. Such changes may be the result of exposure of the cells to environmental toxins.

Moreover, with respect to a extracorporeal bioartificial liver (BAL), the differentiated cells (i.e., the hepatocyte-lineage cells) can be incorporated in one of two ways. For example, the cells can be recovered following depolymerization, and seeded to the surface of a flat-plate bioreactor based BAL. Alternatively, the cells can be maintained in the bead environment and the beads can be introduced into a hollow-fiber bioreactor based BAL.

Kits

The present invention provides a kit. In one embodiment, the kit includes a single cell suspension of embryonic stem cells encapsulated within an alginate polyelectrolyte microenvironment. The encapsulated ES cells in the kit are capable of differentiating within the alginate polyelectrolyte microenvironment into hepatocyte lineage cells in the absence of embryoid body intermediates or growth factor supplementation. In one embodiment, this alginate polyelectrolyte microenvironment may be in the form of a polymerized bead.

It is anticipated that the kit may further include other components, such as buffers or divalent cation solutions to facilitate depolymerization of the beads and cell recovery. Suitable buffers and divalent cation solutions include those described under the heading "depolymerization and Cell Recovery" in Example 1. The kit could also include ES cell specific media (e.g., DMEM containing ESGRO) or hepatocyte specific media (e.g., Iscove's media, LIF-free).

Furthermore, the kit may include antibodies specific for cell surface markers on ES cells and/or antibodies to detect cell surface markers on hepatocyte lineage cells. Non-limiting examples of ES cell markers and hepatocyte markers are described above, and antibodies specific for these markers are well known in the art. In particular, assessment of the binding of an antibody to an antigen, the expression of which is characteristic of a cellular phenotype or differentiation stage, is useful to assess differentiation.

Methods of Use

The present invention also provides methods suitable for promoting differentiation of embryonic stem cells into functional hepatocytes. In one embodiment, the method includes encapsulating a single cell suspension of ES cells within an alginate polyelectrolyte microenvironment; and culturing the encapsulated cells in differentiation cell media. This method further includes allowing the encapsulated ES cells to differentiate into hepatocyte lineage cells in the absence of embryoid body intermediates or growth factor supplementation.

As described above, differentiation cell media is any cell media that promotes differentiation of cells. In the present instance, a useful differentiation cell media would be one that promotes differentiation of the encapsulated ES cells into hepatocyte-lineage cells. For example, in one embodiment, the differentiation cell media is free of a differentiation inhibitory factor. In one particular embodiment, the differentiation cell media is leukemia inhibitory factor (LIF)-free.

In one embodiment of the method for promoting differentiation of ES cells into functional hepatocytes, the alginate polyelectrolyte microenvironment includes poly-L-lysine. In a further embodiment of this method, the alginate polyelectrolyte microenvironment includes a divalent cation, such as $Ca^{2+}$ or $Ba^{2+}$.

To promote differentiation of the ES cells into functional hepatocytes, the alginate polyelectrolyte microenvironment may preferably be in the form of a polymerized bead. The present inventors have optimized various parameters in the encapsulation process to both induce ES cell differentiation into hepatocytes, and increase function of the hepatocytes. For example, in one embodiment, the bead size is about 500 µm. In another embodiment, the bead is formed at a cell seeding density of about $5\times10^6$ cells per ml. In yet another embodiment, the bead is formed at an alginate concentration of about 2.0% (w/v).

The present inventors have found that alginate-PLL microencapsulation is useful for directing the differentiation of embryonic stem cells into hepatocytes. The mature hepatocyte function was induced in the absence of both growth factor supplementation and embryoid body culture. In one embodiment, the alginate polyelectrolyte microenvironment maintains the encapsulated cells in the hepatocyte differentiated state.

The hepatocyte differentiation method of the present invention allows functional hepatocytes to be recovered from the beads without significant loss in cell viability. The present inventors have established a reversible alginate-PLL microencapsulation culture protocol that may be scaled to produce large quantities of the mature hepatocytes.

As described above, the alginate polyelectrolyte microenvironment maintains the encapsulated cells in the hepatocyte differentiated state. Thus, the present invention further provides a method for maintaining a hepatocyte differentiated state. In one embodiment, this method includes culturing encapsulated single embryonic stem cells in differentiation cell media, wherein the encapsulated ES cells are encapsulated within an alginate polyelectrolyte microenvironment. The method further includes allowing the cultured encapsulated ES cells to differentiate into hepatocyte lineage cells in the absence of embryoid body intermediates or growth factor supplementation. Furthermore, the method includes maintaining the hepatocyte differentiated state of the cells by maintaining the encapsulated differentiated cells in the differentiation cell media.

As mentioned above, the differentiation cell media is any cell media that promotes differentiation of cells. In the present method for maintaining a hepatocyte differentiated state, the differentiation cell media promotes differentiation of the ES cells into hepatocyte-lineage cells. In one embodiment, the differentiation cell media may be free of a differentiation inhibitory factor, which is a substance which acts to maintain an undifferentiated phenotype of cells.

In one embodiment of the method for maintaining a hepatocyte differentiated state, the alginate polyelectrolyte microenvironment may be in the form of a polymerized bead. This bead may be formed at an alginate concentration of from about 1.7% (w/v) to about 2.5% (w/v). In one embodiment, the bead size is about 500 µm.

In another embodiment of the method for maintaining a hepatocyte differentiated state, the alginate polyelectrolyte microenvironment includes poly-L-lysine. In a further embodiment of this method, the alginate polyelectrolyte microenvironment includes a divalent cation. Suitable divalent cations can include $Ca^{2+}$ or $Ba^{2+}$.

Another aspect of the present invention relates to methods for increasing the yield of embryonic stem cells. In particular, the present inventors have found that a suitable alginate polyelectrolyte microenvironment is useful for increasing the yield of embryonic stem cells.

In one embodiment, a method for increasing the yield of embryonic stem cells includes encapsulating a single cell suspension of ES cells within an alginate polyelectrolyte microenvironment that includes a polymerized bead formed as an alginate concentration of from about 1.% (w/v) to about 2.5% (w/v). This method further includes culturing the encapsulated cells in cell media including a differentiation inhibitory factor to maintain an undifferentiated phenotype for the encapsulated cells; and allowing the encapsulated undifferentiated ES cells to expand in culture while in the presence of the differentiation inhibitory factor. As mentioned above, a differentiation inhibitory factor is a substance which acts to maintain an undifferentiated phenotype cell. An example of a differentiation inhibitory factor is leukemia inhibitory factor (LIF).

In one embodiment of the method for increasing the yield of embryonic stem cells, the alginate polyelectrolyte microenvironment includes poly-L-lysine. In another embodiment, the alginate polyelectrolyte microenvironment includes a divalent cation. Moreover, the alginate polyelectrolyte microenvironment may be in the form of a polymerized bead, which is of a size of about 500 µm.

The method for increasing the yield of embryonic stem cells can further include the step of depolymerizing the bead in the presence of a chelating agent. The depolymerization may occur after the encapsulated undifferentiated ES cells have been allowed to expand in culture while in the presence of the differentiation inhibitory factor. The depolymerizing may include removing the cell media including the differentiation inhibitory factor; washing the beads; and adding to the washed beads a solution including a chelating agent.

Method for Producing

The present invention is further directed to methods for producing encapsulated embryonic stem cells. In one embodiment, the method includes providing a single cell suspension of ES cells; and combining this single cell suspension of ES cells with an alginate solution to form a mixture. This method further includes subjecting the mixture to an electrostatic field to form electrostatic alginate droplets; and exposing the electrostatic alginate droplets to a divalent cation solution to form a bead about the ES cells. The method also includes allowing the bead to polymerize in the presence of the divalent cation solution; and contacting the polymerized bead with a polyelectrolyte solution.

As described above, the present inventors have optimized various parameters in the encapsulation process to both induce ES cell differentiation into hepatocytes, and increase function of the resulting hepatocytes. For example, in one embodiment, the final cell density after the combining step is about $1 \times 10^6$ cells per ml to about $1 \times 10^7$ cells per ml. In another embodiment, the final cell density after the combining step is about $5 \times 10^6$ cells per ml.

The alginate concentration may range from about 1.7% (w/v) to about 2.5% (w/v). In one embodiment, the alginate concentration after the combining step is about 2.0% (w/v).

Furthermore, in one embodiment, the polyelectrolyte solution with which the polymerized bead is contacted includes poly-L-lysine. In another embodiment, the concentration of the poly-L-lysine during the contacting step is about 0.05% (w/v).

Figure 1:
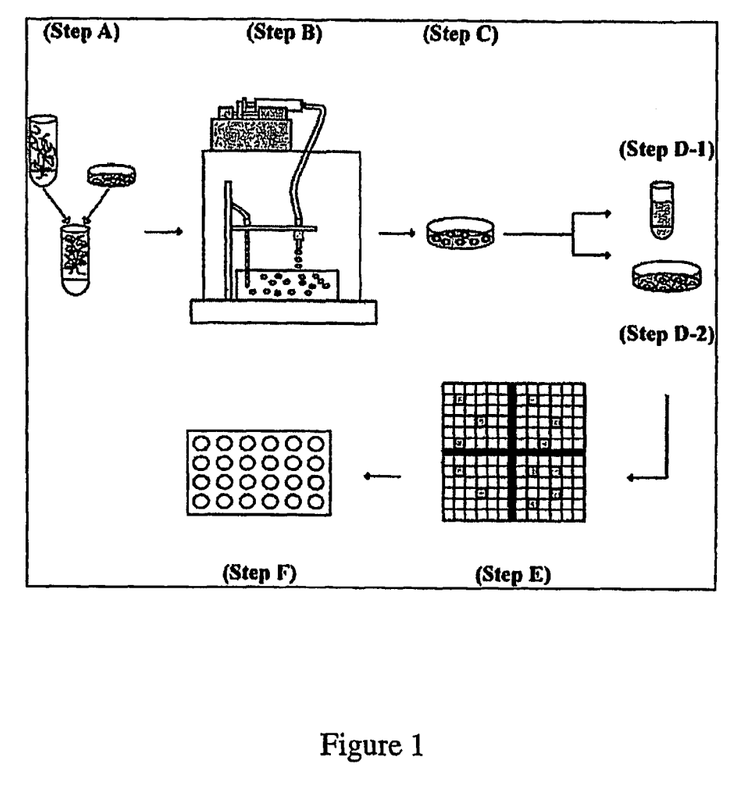
FIG. 1 is a schematic representation of an encapsulation procedure according to the present invention and an analysis procedure.

FIG. 1 is a schematic representation of one embodiment of an encapsulation procedure according to the present invention. FIG. 1 also shows an analysis procedure useful for assessing the encapsulated cell population, and the cells recovered following the depolymerization of the beads. This figure is described below in Example 2.

EXAMPLES

Example 1

Materials and Methods

Cell Culture

All cell cultures were incubated in a humidified 37° C., 5% $CO_2$ environment. The ES cell line D3 (ATCC, Manassas, Va.) was maintained in an undifferentiated state in T-75 gelatin-coated flasks (Biocoat, BD-Biosciences, Bedford, Mass.) in Knockout Dulbecco's modified Eagles medium (Gibco, Grand Island, N.Y.) containing 15% knockout serum (Gibco), 4 mM L-glutamine (Gibco), 100 U/ml penicillin (Gibco), 100 U/ml streptomycin (Gibco), 10 µg/ml gentamicin (Gibco), 1000 U/ml ESGRO (Chemicon, Temecula, Calif.), 0.1 mM 2-mercaptoethanol (Sigma-Aldrich, St. Louis, Mo.). ESGRO contains leukemia inhibitory factor (LIF) which prevents embryonic stem cell differentiation. Every 2 days, media was aspirated and replaced with fresh media. Cultures were split and passaged every 6 days, following media aspiration, washing with 6 ml of phosphate buffered solution (PBS) (Gibco). Cells were detached following incubation with 3 ml of trypsin (Gibco) for three minutes, resulting in a single cell suspension, and subsequently the addition of 12 ml of Knockout DMEM. Cells were then replated in gelatin-coated T-75 flasks at a dilution of 1:15 and only passages 10-22 used in the experiments. In order to induce differentiation, cells were suspended in Iscove's modified Dulbecco's medium (Gibco) containing 20% fetal bovine serum (Gibco), 4 mM L-glutamine (Gibco), 100 U/ml penicillin, 100 U/ml streptomycin (Gibco), 10 µg/ml gentamicin (Gibco). The Hepa 1-6 cell line (ATCC, Manassas, Va.) was maintained in Dulbecco's modified Eagles medium (Gibco) containing 10% fetal bovine serum (Gibco), 100 U/ml penicillin (Gibco), 100 U/ml streptomycin (Gibco), and 4 mM L-glutamine (Gibco). Hepa1-6 cells were grown on tissue culture treated T-75 flasks (Falcon, BD Biosciences, San Jose, Calif.), and passages 10 through 22 were utilized for the experiments.

Alginate Poly-L-Lysine Encapsulation

An alginate solution was generated by dissolving 2.2 g of alginate (Sigma-Aldrich, MW: 100,000-200,000, G-content 65-70%) in 100 ml of $Ca^{2+}$ free DMEM (Gibco), using a heated magnetic stir plate at a temperature of 45° C. The solution was then filtered using a 25 micron syringe filter (Fisher Brand, Pittsburgh, Pa.). A confluent monolayer of adherent cells was removed following trypsin incubation, as described above, centrifuged for 10 minutes at 1200 rpm, and resuspended in PBS. The cells were washed twice more with PBS (Gibco), resuspended in 2 ml of their respective media and both cell number and viability assessed using the method of trypan blue (Gibco) exclusion.

For the base-line conditions, a 1 ml aliquot of cell suspension with a seeding density of $5 \times 10^7$ cells/ml was added to 9 ml of a 2.2% (w/v) alginate solution to yield a final cell seeding density of $5 \times 10^6$ cells/ml and a final alginate concentration of 2.0% (w/v), FIG. 1, Step A. This solution was transferred to a 10 ml syringe (BD Biosciences) which, in turn, was connected to a syringe pump (KD Scientific, Holliston, Mass.). Alginate beads were generated using an electrostatic bead generator (Nisco, Zürich, Switzerland) at a flow rate of 40 ml/hour, and an applied voltage of 6.5 kV, resulting in beads with a diameter of 500 µm. The beads were extruded into a 200 ml bath of $CaCl_2$ (100 mM) (Sigma-Aldrich), containing 145 mM NaCl (Sigma-Aldrich), and 10 mM MOPS (Sigma-Aldrich) and were left to polymerize for 10 minutes at room temperature, FIG. 1, Step B. Beads were transferred to a tissue culture treated T-25 flask (Falcon, BD Biosciences), following the polymerization step. The $CaCl_2$ solution was removed using a 5 ml pipette, and the beads were washed with 5 ml of Hepes (Gibco). The Hepes was removed and the beads were resuspended in 5 ml of poly-L-lysine (PLL) (Sigma-Aldrich, MW: 68,600 g/mol) (0.05% w/v) for 2 minutes. The PLL was then gently removed, replaced with Hepes to wash the beads and the beads were ultimately resuspended into cell culture media, FIG. 1, Step C.

Media was changed at days 4, 8, 11, 14, 17 post encapsulation. Viability within beads was assessed with, a calcein (Molecular Probes, Eugene, Oreg.), ethidium homodimer (Molecular Probes) stain. Calcein and ethidium homodimer images were acquired using a computer interfaced Olympus IX70 microscope (Melville, N.Y.) fitted with a 495 nm excitation filter and emission filters of 515 nm and 635 µm, respectively. Digitized images were quantified using Olympus Microsuite. In all experimental conditions, seven day monolayer culture configurations of Hepa1-6 cells, previous to plate overgrowth, were used as controls for viability, growth kinetics, and functional studies.

Formation of Embryoid Body Control

Embryoid bodies (EB) were formed (day 0) and cultured for two days using the hanging drop method ($1 \times 10^3$ ES cells per 30 µl drop). Hanging drops were transferred to suspension culture (day 2) in 100 mm petri dishes (Falcon, BD Biosciences) and cultured for an additional 2 days. The EBs were then plated (day 4), one EB per well, in tissue culture treated 6 well plates (Falcon, BD Biosciences). Media was changed at days 8, 11, 13 post induction of differentiation (day 0). Analysis of the EB system was limited to days 8, 11, 14, and 17, being that the EBs overgrow the well plate following day 17.

Depolymerization and Cell Recovery

Indirect immunofluorescent analysis and aggregate size calculations (see below) were performed following the release of cells from the beads, FIG. 1, Step D-2. A minimum of 1,500 beads were analyzed per replicate per condition. Beads were washed with PBS, and 100 mM sodium citrate (Fisher Scientific), containing 10 mM MOPS (Sigma-Aldrich), and 27 mM NaCl (Sigma-Aldrich) was added for 30 minutes at 37° C. to induce depolymerization. This method results in 98% recovery of the encapsulated cell population. The released cells were centrifuged at 1200 rpm for 10 minutes, the sodium citrate solution was aspirated, the cell pellet was washed with PBS (3×), and resuspended in cell specific media. The cells were then counted using the aforementioned trypan blue method, FIG. 1, Step E.

In Situ Indirect Immunofluorescent Albumin Analysis

Cells recovered following depolymerization were transferred to a tissue culture treated 24 well plate (Falcon, BD Biosciences, FIG. 1, Step E). Specifically, the isolated cell population was diluted to $6 \times 10^4$ cells in 0.75 ml of media, and was incubated for one hour at 37° C. to induce cell attachment. The following procedure applies to both the EB system (control), as well as cells recovered following polymerization. The cells were then washed for 10 min in cold PBS and fixed in 4% paraformaldehyde (Sigma-Aldrich) in PBS for 15 minutes at room temperature. The cells were washed twice for 10 min in cold PBS and then twice for 10 min in cold saponine/PBS (SAP) membrane permeabilization buffer containing 1% bovine serum albumin (BSA) (Sigma-Aldrich), 0.5% saponine (Sigma-Aldrich) and 0.1% sodium azide (Sigma-Aldrich). The cells were subsequently incubated for 30 minutes at 4° C. in a SAP solution containing rabbit anti-mouse albumin antibody (150 µg/ml) (MP Biomedicals, Irvine, Calif.), or normal rabbit serum (150 µg/ml) (MP Biomedicals) as an isotype control, washed twice for 10 min in cold SAP buffer, and then treated for 30 minutes at 4° C. with the secondary antibody, FITC-conjugated donkey anti-rabbit, diluted 1:500 (Jackson Immuno Labs, Westgrove, Pa.). Cells were then washed once with cold SAP buffer and once with cold PBS. Fluorescent images were acquired using a computer-interfaced inverted Olympus IX70 microscope. Specimens were excited using a 515 nm filter. Fluorescent intensity values were determined for each cell using Olympus Microsuite. Experimental intensity values for each cell were calculated after subtracting the average intensity of the isotype control.

Image Analysis Sample Size

The minimum sample size required for calcein ethidium homodimer analysis of intracapsular viability and indirect immunofluorescent analysis of intracellular albumin was determined using Minitab Release 13, English Version (Minitab Inc., State College, Pa.). The two-tailed two-sample t-test mode of the power algorithm was used with a population standard deviation of 5, to allow for large sample variation, a power value of 0.8, a significance level of 0.05, and a minimum difference (effect) of 3, for fine resolution between population means. The resultant minimum sample size that was calculated was 45 cells. To ensure this sample size, 2 images (fields) were acquired per sample, and a minimum of 30 cells per image were quantified.

Urea Analysis

Media samples were collected directly from encapsulated cell cultures on days 8, 11, 14, 17, and 20 post encapsulation, FIG. 1, Step D-1, and stored at −20° C. for subsequent urea content analysis. Media samples were collected from the EB System (control) on days 8, 11, 14, 17 post induction of differentiation, and stored at −20° C. for subsequent urea content analysis. Urea synthesis was assayed using a commercially available kit (StanBio, Boerne, Tex.). A standard curve was generated by creating serial dilutions of a urea standard from 300 µg/ml to 0 µg/ml. Absorbance readings were obtained using a Biorad (Hercules, Calif.) Model 680 plate reader with a 585 nm emission filter. Urea values were normalized to cell counts obtained on the day of media sample collection.

Aggregate Cell Number

Cells recovered following depolymerization ($6 \times 10^4$) were transferred to a tissue culture treated 24 well plate and allowed to adhere for one hour at 37° C. Bright field images were captured using a computer-interfaced inverted Olympus IX70 microscope. Images were quantified using Olympus Microsuite. In short, a color threshold was first applied in order to distinguish cellular aggregates from the image background. A region of interest was then established for each aggregate, and the number of cells per aggregate was determined using particle size filters based on diameter.

Statistical Analysis

Each data point represents the mean, and the error bars represent the standard error of the mean. Statistical significance was determined using the student t-test for unpaired data. Differences were considered significant when the probability was less then, or equal to, 0.05. Each experiment was repeated a minimum of three times, with a minimum of three replicates per experiment.

Example 2

Encapsulation System

An alginate-PLL murine embryonic stem cell encapsulation system was developed in order to investigate the feasibility of regulating hepatocyte differentiation within a controlled microenvironment and recovering differentiated cells from intracapsular culture. One embodiment of the encapsulation system is shown in FIG. 1. Briefly, embryonic stem cells were detached from culture dishes and mixed with various concentrations of dissolved alginate (Step A). The alginate cell suspension mixture was transferred to a 10 ml syringe within an electrostatic bead generator (Step B), which was used to control bead size through an applied voltage (6.5 kV). The alginate cell suspension was extruded into a bath of 100 mM calcium chloride and the beads were subsequently coated in a poly-L-lysine solution to increase bead durability. The encapsulated cell population was then cultured for 20 days, either in the presence or absence of LIF (Step C). On days 8, 11, 14, 17 and 20 post encapsulation, media samples were removed (Step D-1) for urea analysis, and the beads were subsequently depolymerized using sodium citrate (Step D-2) to recover the cells. The cells were then transferred to a 24 well plate for subsequent intracellular albumin and aggregate size analyses.

Example 3

Assessment of Biocompatibility

Initial experiments were designed to determine the biocompatibility of alginate-PLL microencapsulation using both Hepa1-6 murine hepatoma cells and undifferentiated murine embryonic D3 cells. Immediately following encapsulation, beads were stained with calcein/ethidium homodimer, imaged, and the number of viable cells within the beads determined. On average, the percent viability was reduced minimally from 98% to 95%, indicating that the encapsulation process caused little cell damage. The effect of depolymerization and recovery on cell viability was also assessed.

Figure 2:
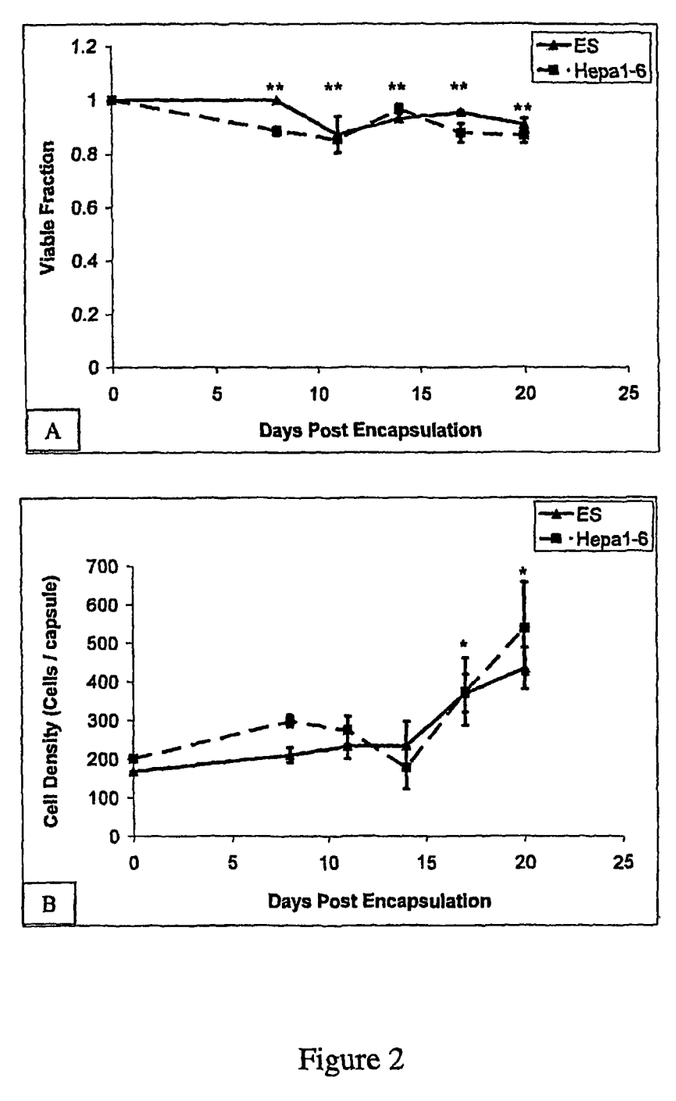

The results are shown in FIG. 2 (A and B). In these experiments, ES cells were encapsulated in 2.0% w/v alginate, at a cell seeding density of $5 \times 10^6$ cells/ml, and cultured in Knockout DMEM containing ESGRO to prevent differentiation; Hepa 1-6 cells were encapsulated in 2.0 w/v alginate, at a cell seeding density of $5 \times 10^6$ cells/ml, and cultured in DMEM. In FIG. 2, each data point represents the mean of a sample size of three, and error bars represent standard error of the mean. Double asterisks (**) indicates that no statistically significant difference exists for a time point as compared to other time points for both ES cells and Hepa1-6 cells. Asterisks (*) designate a statistically significant difference (p<0.05) for a time point as compared to day 0 for both ES cells and Hepa1-6 cells.

As shown in FIG. 2A, viability of encapsulated ES cells and Hepa1-6 cells was maintained at greater than 90% throughout the 20 day study. Growth kinetic studies (FIG. 2B), indicated that both encapsulated ES cells and Hepa1-6 cells, following an initial lag phase, began to proliferate at approximately 14 days post encapsulation. In the case of ES cells, they ultimately reached a final density of 433 cells/bead, about 2.5 times greater then the initial density (168 cells/bead). Hepa1-6 cells reached a final density of 537 cells/bead, approximately 2.6 times higher then the initial density (206 cells/bead). These results indicate that neither encapsulation nor depolymerization significantly affected cell viability.

Example 4

Evaluation of Mature Hepatocyte Function

Figure 3:
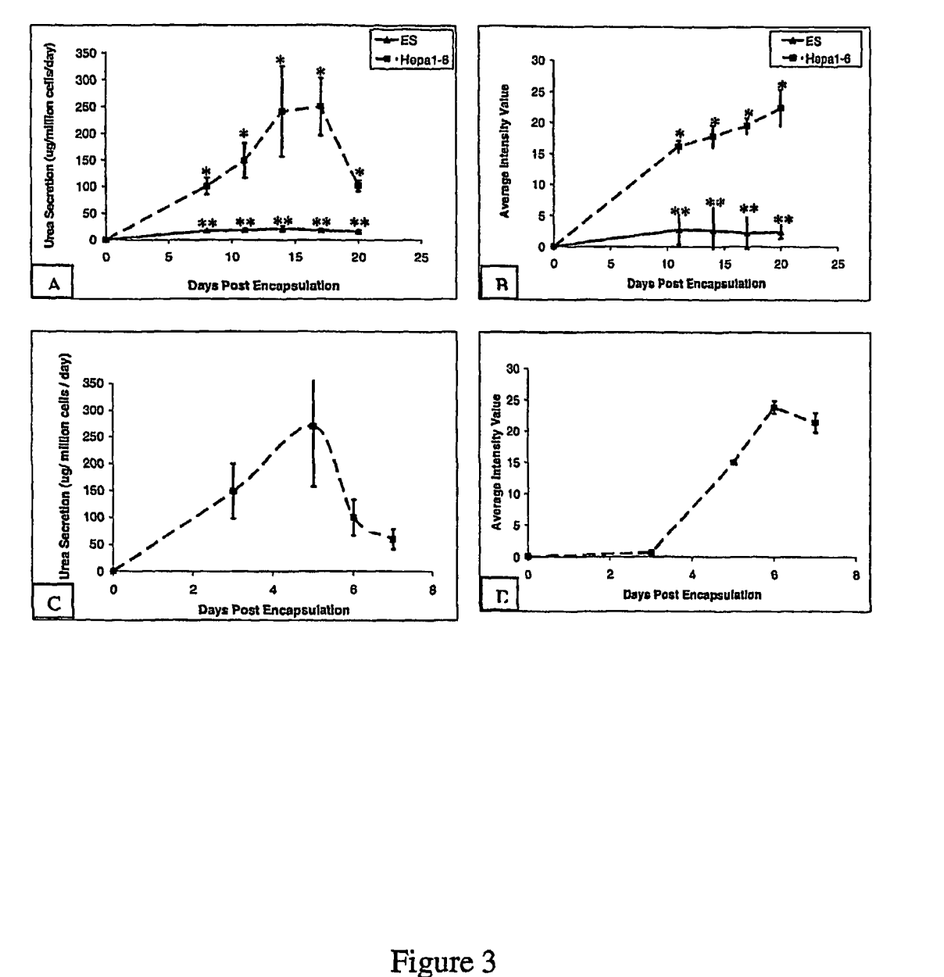

Cell function following alginate encapsulation was evaluated. Two hepatocyte specific functions were assessed, urea secretion and intracellular albumin synthesis. The results are shown in FIG. 3 (A and B), where urea secretion was quantified using a commercially available kit and intracellular albumin synthesis was quantified using indirect immunofluorescence in conjunction with digital microscopy and image analysis. It is noted that albumin was also secreted from the cells.

In these experiments, ES cells were encapsulated in 2.0% w/v alginate, at a cell seeding density of $5 \times 10^6$ cells/ml, and cultured in Knockout DMEM containing ESGRO to prevent differentiation; Hepa 1-6 cells were encapsulated in 2.0% w/v alginate, at a cell seeding density of $5 \times 10^6$ cells/ml, and cultured in DMEM. Each data point in FIG. 3 represents the mean of a sample size of three, and error bars represent standard error of the mean. Asterisks (*) designate a statistical difference between ES cells and Hepa1-6 cells (p<0.05). Double asterisks (**) indicate no statistical change in ES function at a time point as compared to other time points.

As seen in FIG. 3A, while encapsulated Hepa1-6 cells exhibited significant levels of urea secretion during the 20 day culture period, undifferentiated ES cells maintained in LIF containing media, did not. In addition, albumin synthesis was supported in the Hepa1-6 cell population, whereas no significant albumin production was detected in the LIF supplemented ES cell population (FIG. 3B). Thus, encapsulation was able to support mature hepatocyte function in differentiated cells, with levels of Hepa1-6 function comparable to average values obtained in 7 day monolayer Hepa1-6 cultures, previous to plate overgrowth, for urea secretion (FIG. 3C) and intracellular albumin production (FIG. 3D), but did not promote differentiation in LIF supplemented ES cell populations.

Example 5

Alginate Encapsulation and Embryonic Stem Cell Differentiation Culture

Subsequent studies were conducted to assess whether ES cells encapsulated in alginate-PLL beads would differentiate into hepatocytes or hepatocyte-like cells. Beads formed at a final cell concentration of $5 \times 10^6$ cells/ml (168 cells/bead) and an alginate concentration of 2.0% (w/v) were cultured in LIF-free media (e.g., Iscove's media), and cell viability and growth kinetics assessed.

Figure 4:
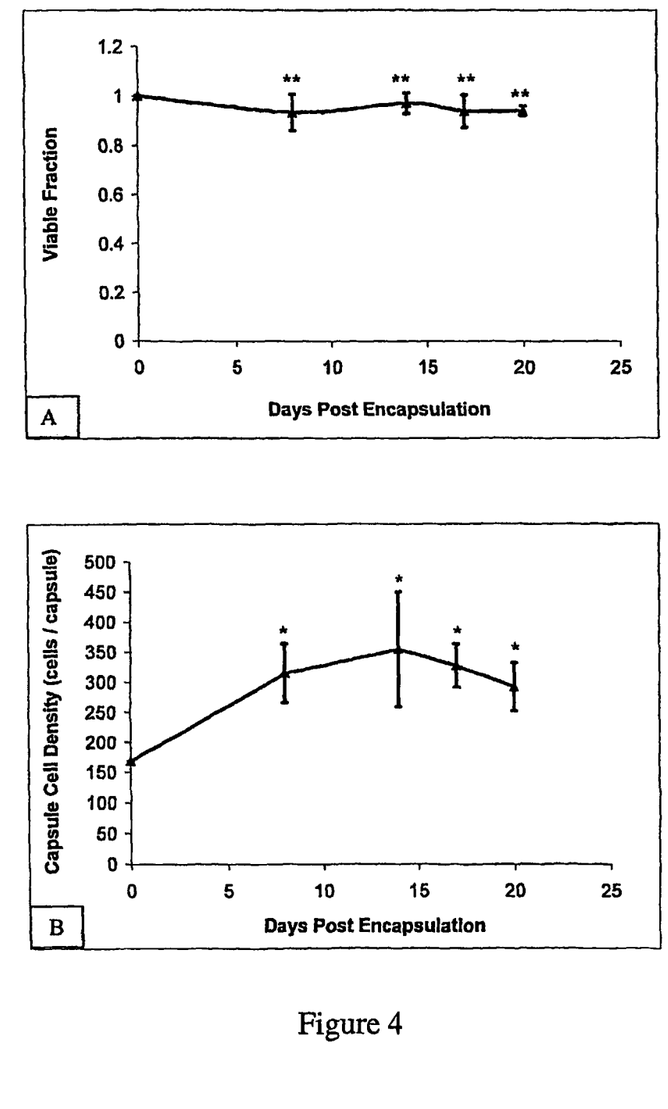

The results are shown in FIG. 4 (A and B), where each data point represents the mean of a sample size of fifteen, and error bars represent standard error of the mean. Double asterisks (**) indicate no statistical change in viability at a time point as compared to other time points. Asterisks (*) indicate a statistically significant difference (p<0.05) from day 0.

As shown in FIG. 4A, the ES cell population maintained greater then 95% viability and cells continued to divide during the first 10-15 days of culture. The maximal cell number was observed at day 14 post encapsulation (FIG. 4B), as the ES population reached a density of 291 cells/bead and remained constant thereafter.

Figure 5:
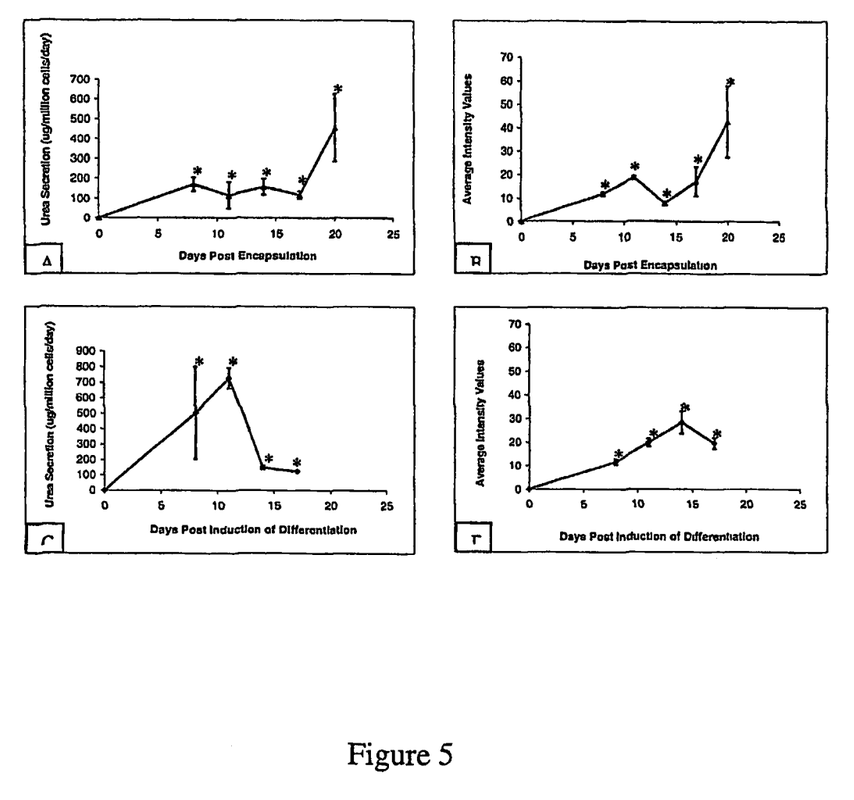

Hepatocyte function of encapsulated ES cells was evaluated by measuring urea secretion and albumin synthesis. The results are shown in FIG. 5 (A and B). In these experiments, the ES cells were encapsulated in 2.0% w/v alginate at a cell seeding density of $5 \times 10^6$ cells/ml, and cultured in LIF-free media (e.g., Iscove's media) before being evaluated. In FIG. 5, each data point represents the mean of a sample size of fifteen, and error bars represent standard error of the mean. Asterisks (*) indicate statistically significant differences (p<0.05) from day 0.

The results of urea secretion studies are summarized in FIG. 5A and indicate that urea secretion was detected as early as day 8 following encapsulation, and maximum function (458 μg/$10^6$ cells/day) was detected at day 20 post encapsulation. As indicated in FIG. 5B, albumin synthesis followed the same kinetic trend. Albumin was detected by day 8 post encapsulation and reached a maximum level of expression at day 20. Thus alginate encapsulation could not only support ES cell viability and growth, but could also promote ES cell differentiation into hepatocyte lineage cells. Additionally, the encapsulation system yielded maximum functional values comparable to the EB differentiation system (urea secretion: 727 μg/106 cells/day; intracellular albumin production: 28.35), and maintained these values, whereas function decreases over time in the EB system. Panels C and D in FIG. 5 depict the embryoid body control for urea and intracellular albumin production, respectively.

Example 6

Modulation of Differentiated Function Through Alterations in Cell Seeding Density and Alginate Concentration Having established the kinetics of encapsulated differentiation, the next set of studies was designed to test whether differentiation, as measured by hepatocyte function, could be modulated through alterations in two key bead parameters, 1) cell seeding density, and 2) alginate concentration.

Figure 6:
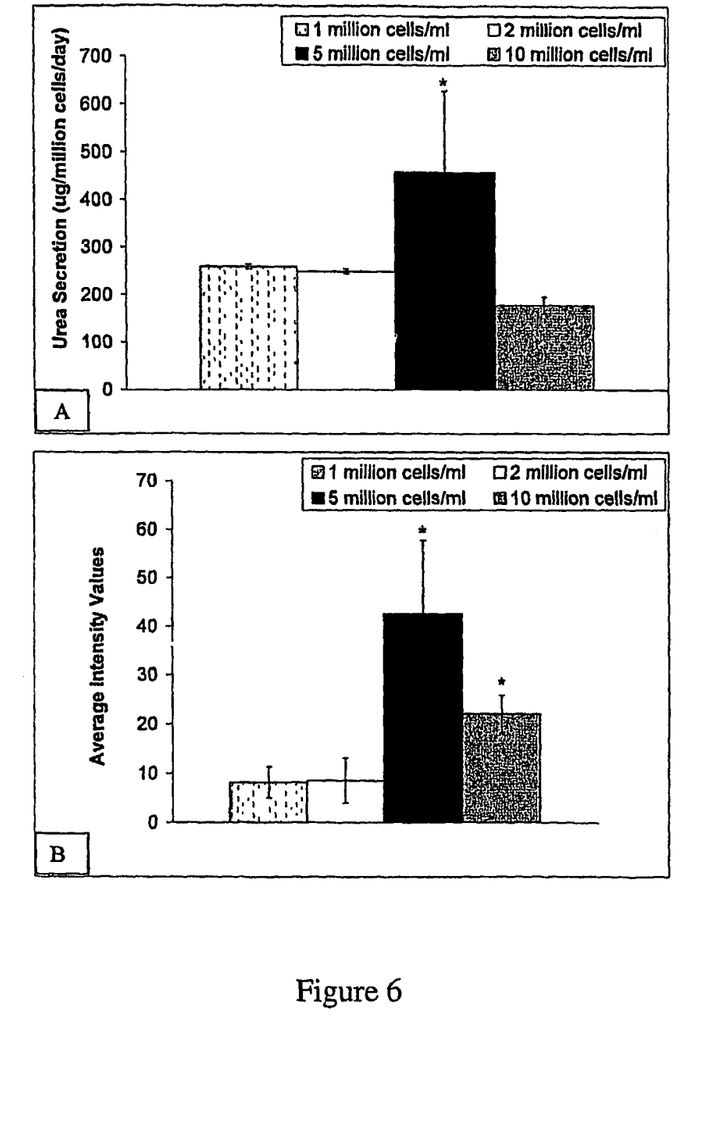

The results are shown in FIG. 6 (A and B). Initial ES cell seeding densities of $1 \times 10^6$ cells/ml, $2 \times 10^6$ cells/ml, $5 \times 10^6$ cells/ml, and $1 \times 10^7$ cells/ml were generated in a constant 2.0% alginate concentration, and the encapsulated cell population, cultured in LIF-free media (e.g., Iscove's media) was assayed for urea secretion (A) and intracellular albumin production (B) at day 20. In FIG. 6, each data point represents the mean of a sample size of nine, and error bars represent standard error of the mean. Asterisks (*) indicate statistically significant differences (P<0.05) from the conditions of $1 \times 10^6$ cells/ml and $2 \times 10^6$ cells/ml at day 20.

Maximum urea secretion was observed with an initial seeding density of $5\times10^6$ cells/ml, and yielded 458 µg/$10^6$ cells/day (approximately two times higher then the values obtained for the other cell seeding densities that were tested). Intracellular albumin results followed a similar trend as an initial cell seeding density of $5\times10^6$ cells/ml exhibited an average intensity value, which was 150% greater than the other seeding conditions.

The effect of alginate concentration on functional modulation was examined by generating three different alginate concentrations (1.7% w/v, 2.0% w/v, and 2.5% w/v) while holding both the ES cell seeding density ($5\times10^6$ cells/ml) and the applied voltage (6.5 kV) constant. Voltage consistency ensured that the bead diameter would remain unchanged regardless of the alginate concentration used. Alginate concentrations were bounded between 1.7% (w/v) and 2.5% (w/v) due to the formation of tails at concentrations lower than 1.7% (w/v), and no observed cell proliferation above 2.5% (w/v) (data not shown). The cells were cultured in Iscove's media, which was LIF-free.

Figure 7:
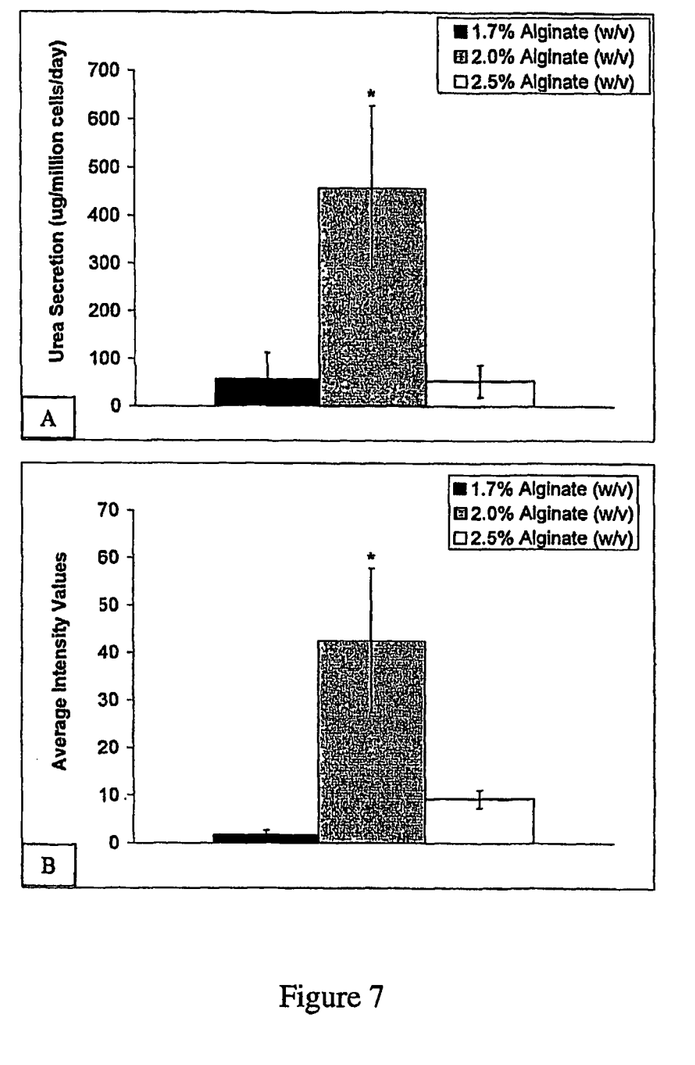

The results of these studies are presented in FIG. 7 (A and B), where each data point represents the mean of a sample size of nine, and error bars represent standard error of the mean. Asterisks (*) indicate a statistically significant difference from other conditions at day 20. These results indicate that encapsulation with 2.0% alginate resulted in a marked increase in function relative to the other alginate concentrations studied. Urea secretion (A) was approximately nine times higher then values obtained for 1.7% alginate (58 ug/$10^6$ cells/day), and 2.5% alginate (44 ug/$10^6$ cells/day). Intracellular albumin production (B) at day 20 was also significantly higher in cells encapsulated with 2.0% alginate.

A subsequent set of studies was performed to assess the distribution of functional cells within the population of differentiated cells. Following bead depolymerization and cell recovery, cells were fixed, and the number of albumin expressing cells evaluated using indirect immunofluorescence (Table 1 below).

TABLE 1

Population Characterization of Encapsulated Cell Populations Subjected to Changes in Cell Seeding Density and Alginate Concentration

| Alginate Concentration (w/v) | Cell Seeding Density | Day 20 Percent of Population Positively Stained | Day 20 Average Fluorescence Intensity for Positive Cells |
|---|---|---|---|
| 2.0% | $1 \times 10^6$ | 31 ± 2 | 8.19 ± 3.17 |
| 2.0% | $2 \times 10^6$ | 35 ± 1 | 8.52 ± 4.62 |
| 2.0% | $5 \times 10^6$ | 87 ± 3 (*) | 42.62 ± 15.19 (*) |
| 2.0% | $1 \times 10^7$ | 72 ± 3 (*) | 22.04 ± 3.80 (*) |
| 1.7% | $5 \times 10^6$ | 35 ± 1 | 1.70 ± 0.94 (*) |
| 2.5% | $5 \times 10^6$ | 64 ± 2 (*) | 9.20 ± 1.86 |

In Table 1, positively stained cells were characterized as exhibiting intensity levels higher then the average intensity value determined for the isotype control. Each data point represents the mean of a sample size of nine, and error bars represent standard error of the mean. Asterisks (*) indicate statistical significance from all other conditions (p < 0.05).

As shown in Table 1, as cell seeding density was increased to the optimal value of $5\times10^6$ cells/ml, the percentage of cells expressing intracellular albumin increased as well. In addition, increases in fluorescence intensity values, corrected for non-specific binding using isotype control measurements, indicate that the level of intracellular albumin per cell increased as a function of initial cell seeding density, with the maximum value at to $5\times10^6$ cells/ml. Changes in alginate concentration also had similar effects, with the condition of 2.0% alginate, exhibiting both the highest average intensity for intracellular albumin, and the highest percentage of positively stained cells.

Finally, the effect of cell seeding density and alginate concentration modulation on the encapsulated cell population was also evaluated by examining the generation of cell aggregates. The cell population recovered following depolymerization was quantified by evaluating cell aggregate size (Table 2 below).

TABLE 2

Average aggregate size of encapsulated cell populations subjected to changes in cell seeding density and alginate concentration.

| Alginate Concentration (w/v) | Cell Seeding Density | Day 20 Average Aggregate Size (cells/aggregate) |
|---|---|---|
| 2.0% | $1 \times 10^6$ | 1.13 ± 0.13 |
| 2.0% | $2 \times 10^6$ | 1.57 ± 0.30 |
| 2.0% | $5 \times 10^6$ | 3.83 ± 0.34 (*) |
| 2.0% | $1 \times 10^7$ | 5.31 ± 0.49 (*) |
| 1.7% | $5 \times 10^6$ | 1.8 ± 0.09 |
| 2.5% | $5 \times 10^6$ | 1.24 ± 0.14 |

Each data point in Table 2 represents the mean of a sample size of nine, and error bars represents the mean of a sample size of nine, and error bars represent standard error of the mean. Asterisks (*) indicate statistical significance from all other conditions (p < 0.05).

Bright field images of cells replated following depolymerization were captured digitally, and regions of interest were generated around each cell aggregate. The number of particles (cells) per region of interest was subsequently determined. The results of these studies indicate that as cell seeding density was increased from, $1\times10^6$ cells/ml, to $1\times10^7$ cells/ml, the number of cells per aggregate increased. Furthermore, there were twice as many cells per aggregate in the 2.0% alginate condition as there were in the 1.7% and 2.5% alginate conditions. Therefore, changes in encapsulation parameters can modulate both mature hepatocyte function and intercellular aggregation in a differentiating embryonic stem cell population.

REFERENCES

1. Chan, C., et al. 2004 Liver Transpl. 10(11):1331-42.
2. Susick, R., et al. 2001 Ann NY Acad Sci 944:398-419.
3. Theise, N. 2003 Expert Opin Biol Ther 3(3):403-8.
4. Theise, N. et al. 2000 Hepatology 32(1):11-6.
5. Vessey, C. and de la Hall, P. 2001 Pathology 33(2):130-41.
6. Hamazaki, T. et al. 2001 FEBS Lett 497(1):15-9.
7. Falasca, L. et al. 2001 Cells Tissues Organs 168(3):126-36.
8. Rokstad, A. et al. 2003 Cells Transplant 12(4):351-64.
9. Selden, C. et al. 1998 Artif organs 22(4):308-19.
10. Demetriou, A., et al. 2004 Ann Surg 239(5): 660-7; discussion 667-70.
11. Hochleitner, B., et al. 2005 Artif Organs 29(1): 58-66.
12. Rahman, T., et al. 2004 Artif Organs 28(5): 476-82.
13. Shito, M., et al. 2003 J Surg Res 111(1): 53-62.
14. Tilles, A., et al. 2002 a. J. Hepatobiliary Pancreat Surg 9(6): 686-96.
15. Tilles, A., et al. 2002 b. Technol Health Care 19 (3-4): 177-86.
16. van de Kerkhove, M., et al. 2004 Ann Surg 240(2): 216-30.
17. Yarmush, M., et al. 1992 a. Cell Transplant 1(5): 32341.
18. Yarmush, M., et al. 1992 b. Ann NY Acad Sci 665: 238-52.
19. Zeilinger, K., et al. 2004 Tissue Eng 10 (7-8): 1113-24.
20. Viravaidya, K, et al. 2004 Biotechnol Prog 20(1): 316-23.
21. Xu, J., et al. 2003 Toxicol App Pharmacol 189(2): 112-9.

What is claimed is:

1. An isolated cell population comprising:
a single cell suspension of embryonic stem cells (ES cells) encapsulated within an alginate polyelectrolyte microenvironment, wherein the encapsulated ES cells are capable of differentiating within said microenvironment into hepatocyte lineage cells in the absence of embryoid body intermediates or growth factor supplementation, wherein at least about 80% of the cell population is capable of differentiating into the hepatocyte lineage cells within the alginate polyelectrolyte microenvironment.

2. The cell population of claim 1, wherein the alginate polyelectrolyte microenvironment comprises poly-L-lysine.

3. The cell population of claim 1, wherein the alginate polyelectrolyte microenvironment comprises a divalent cation.

4. The cell population of claim 3, wherein the divalent cation is $Ca^{2+}$ or $Ba^{2+}$.

5. The cell population of claim 1, wherein the ES cells are positive for a cell surface marker selected from the group consisting of SSEA4, Tra-1-60, Tra-1-81, Oct-4 and combinations thereof.

6. The cell population of claim 1, wherein the hepatocyte lineage cells are positive for a cell surface marker selected from the group consisting of CD34, CD38, C-kit and combinations thereof.

7. The cell population of claim 1, wherein the hepatocyte lineage cells produce albumin.

8. The cell population of claim 1, wherein the hepatocyte lineage cells secrete urea.

9. The cell population of claim 1, wherein the hepatocyte lineage cells express a polypeptide selected from the group consisting of cytochrome P450 subunit 1a1, cytochrome P450 subunit 1a2, cytochrome P450 subunit 1b1, cytochrome P450 subunit 2b9, cytochrome P450 subunit 2b13, cytokeratin 18, connexin 32, alpha-fetoprotein, transthyretin, alpha-1-antitrypsin, tyrosine aminotransferase and combinations thereof.

10. The cell population of claim 1, wherein the alginate polyelectrolyte microenvironment is in the form of a polymerized bead.

11. The cell population of claim 10, wherein the bead size is about 500 µm.

12. The cell population of claim 10, wherein the bead is formed at a cell seeding density of about $1 \times 10^6$ cells/ml to about $1 \times 10^7$ cells/ml.

13. The cell population of claim 10, wherein the bead is formed at a cell seeding density of about $5 \times 10^6$ cells/ml.

14. The cell population of claim 10, wherein the bead is formed at an alginate concentration of from about 1.7% (w/v) to about 2.5% (w/v).

15. The cell population of claim 10, wherein the bead is formed at an alginate concentration of about 2.0% (w/v).

16. The cell population of claim 1, wherein the alginate polyelectrolyte microenvironment of the encapsulated ES cells does not promote hepatocyte function in undifferentiated ES cells.

17. The cell population of claim 1, wherein the alginate polyelectrolyte microenvironment of the encapsulated ES cells does promote hepatocyte function in hepatocyte differentiated ES cells.

18. The cell population of claim 1, wherein the embryonic stem cells are reversibly encapsulated.

19. A method for producing encapsulated embryonic stem (ES) cells, comprising:
providing a single cell suspension of ES cells;
combining the single cell suspension of ES cells with an alginate solution to form a mixture;
subjecting the mixture to an electrostatic field to form electrostatic alginate droplets;
exposing the electrostatic alginate droplets to a divalent cation solution to form a bead about the ES cells;
allowing the bead to polymerize in the presence of the divalent cation solution; and
contacting the polymerized bead with a polyelectrolyte solution.

20. The method of claim 19, wherein the polyelectrolyte solution comprises poly-L-lysine.

21. The method of claim 19, wherein the final cell density after the combining step is about from $1 \times 10^6$ cells/ml to about $1 \times 10^7$ cells/ml.

22. The method of claim 19, wherein the final cell density after the combining step is about $5 \times 10^6$ cells/ml.

23. The method of claim 19, wherein the alginate concentration after the combining step is about 2.0% (w/v).

24. The method of claim 20, wherein the concentration of the poly-L-lysine during the contacting is about 0.05% (w/v).

25. A method for increasing the yield of embryonic stem cells, the method comprising:
encapsulating a single cell suspension of ES cells within an alginate polyelectrolyte microenvironment comprising a polymerized bead formed at an alginate concentration of from about 1.7% (w/v) to about 2.5% (w/v);
culturing the encapsulated cells in cell media comprising a differentiation inhibitory factor to maintain an undifferentiated phenotype for the encapsulated cells; and
allowing the encapsulated undifferentiated ES cells to expand in culture while in the presence of the differentiation inhibitory factor.

26. The method of claim 25, further comprising depolymerizing the bead in the presence of a chelating agent after the allowing step.

27. The method of claim 26, further comprising recovering the expanded cells from the depolymerized beads.

28. The method of claim 26, wherein the depolymerizing comprises removing the cell media; washing the beads; and adding to the washed beads a solution comprising the chelating agent.

29. The method of claim 25, wherein the alginate polyelectrolyte microenvironment comprises poly-L-lysine.

30. The method of claim 25, wherein the alginate polyelectrolyte microenvironment comprises a divalent cation.

31. The method of claim 25, wherein the bead size is about 500 µm.

32. A kit comprising:
a single cell suspension of embryonic stem cells (ES cells) encapsulated within an alginate polyelectrolyte microenvironment, wherein the encapsulated ES cells are capable of differentiating within said microenvironment into hepatocyte lineage cells in the absence of embryoid body intermediates or growth factor supplementation.

* * * * *